United States Patent [19]

Dahms

[11] Patent Number: 5,443,759
[45] Date of Patent: Aug. 22, 1995

[54] OIL-IN-WATER EMULSIONS

[75] Inventor: Gerd H. Dahms, Velbert, Germany

[73] Assignee: Tioxide Specialties Limited, London, England

[21] Appl. No.: 24,069

[22] Filed: Mar. 1, 1993

[30] Foreign Application Priority Data

Feb. 29, 1992 [GB] United Kingdom ............. 9204387.6

[51] Int. Cl.$^6$ ............................................. B01J 13/00
[52] U.S. Cl. .................................... 252/302; 252/314
[58] Field of Search .................. 424/59; 252/302, 314; 514/938

[56] References Cited

U.S. PATENT DOCUMENTS

| 4,731,242 | 3/1988 | Palinczar ............................... 424/59 |
| 4,820,508 | 4/1989 | Wortzman ............................. 424/59 |
| 4,917,883 | 4/1990 | Strobridge ............................ 424/59 |
| 5,028,417 | 7/1991 | Bhat et al. ............................. 424/59 |
| 5,041,281 | 8/1991 | Strobridge ............................ 424/59 |
| 5,093,109 | 3/1992 | Mausner ................................ 424/63 |
| 5,169,624 | 12/1992 | Zielger et al. ........................ 424/59 |
| 5,208,012 | 5/1993 | Sudo et al. ............................ 424/59 |
| 5,250,289 | 10/1993 | Boothroyd et al. ................... 424/59 |

FOREIGN PATENT DOCUMENTS

| 1602592 | 11/1992 | Australia . |
| 9216026 | 11/1992 | Australia . |
| 0456458 | 11/1991 | European Pat. Off. . |
| 0456459 | 11/1991 | European Pat. Off. . |
| 0456460 | 11/1991 | European Pat. Off. . |
| 49-00450 | 1/1974 | Japan . |
| 52-72833 | 6/1977 | Japan . |
| 53-124627 | 10/1978 | Japan . |
| 58-043912 | 3/1983 | Japan . |
| 58-062106 | 4/1983 | Japan . |
| 59-062517 | 4/1984 | Japan . |
| 60-149515 | 8/1985 | Japan . |
| 60-149516 | 8/1985 | Japan . |
| 60-149517 | 8/1985 | Japan . |
| 1030637 | 9/1989 | Japan . |
| 5025028 | 2/1993 | Japan . |
| 2217987 | 11/1989 | United Kingdom . |
| 2226018 | 6/1990 | United Kingdom . |
| 2264703 | 9/1993 | United Kingdom . |
| WO9006103 | 6/1990 | WIPO . |
| 9009777 | 9/1990 | WIPO . |
| 9011067 | 10/1990 | WIPO . |
| WO9217159 | 10/1992 | WIPO . |
| 9307854 | 4/1993 | WIPO . |
| 9311742 | 6/1993 | WIPO . |

Primary Examiner—Shean Wu
Attorney, Agent, or Firm—Baker & Botts

[57] ABSTRACT

An oil-in-water emulsion containing 0.5% to 30% metallic oxides having a particle size of less than 0.2 micron, less than 10% total emulsifier, 5% to 30% of an oil phase and at least 60% of an aqueous phase is provided.

The invention also makes available a method of preparing such emulsions in which the emulsion is formed by use of a dispersion in water of the metallic oxide particles.

By comparison with previously known emulsions of this type relatively small quantities of emulsifiers are used and it is possible to use an emulsion system with a low HLB value (e.g. less than 6). Preferably no hydrophilic emulsifiers are used.

The emulsions are suitable for preparing UV-absorbing compositions such as sunscreens, moisturizers and after-sun lotions. The ability to use no, or little, hydrophilic emulsifiers is advantageous since, in, general, these emulsifiers are not biodegradable whereas hydrophobic emulsifiers generally are biodegradable.

29 Claims, No Drawings

OIL-IN-WATER EMULSIONS

This invention relates to oil-in-water emulsions and especially to oil-in-water emulsions containing metallic oxides having a small particle size.

Oil-in-water emulsions containing metallic oxides with a small particle size are known in which the total amount of all emulsifiers present is, typically, 18 to 20 percent by weight of the emulsion. Furthermore, it is normally necessary to ensure a balance between hydrophobic and hydrophilic emulsifiers and the particular balance depends upon the nature of the oil phase of the emulsion.

Typical hydrophilic emulsifiers are ethoxylated compounds which generally utilise relatively complex production methods and which are not easily biodegradable.

It is an object of this invention to provide stable oil-in-water emulsions which overcome some of the disadvantages of known oil-in-water emulsions.

According to the invention an oil-in-water emulsion comprises from 0.5 percent to 30 percent by weight with respect to the total weight of emulsion of particles of a metallic oxide having an average primary particle size of less than 0.2 micron said emulsion containing one or more emulsifiers, said one or more emulsifiers being present in an amount of less than 10 percent by weight with respect to the total weight of emulsion, from 5 percent to 30 percent by weight with respect to the total weight of emulsion of an oil phase and at least 60 percent by weight with respect to total weight of emulsion of an aqueous phase.

Also according to the invention a process for preparing an oil-in-water emulsion comprises mixing an aqueous dispersion of particles of a metallic oxide having an average primary particle size of less than 0.2 micron with one or more emulsifiers and an oil phase under conditions in which an oil-in-water emulsion is formed wherein the total amount of emulsifiers present in the oil-in-water emulsion so formed is less than 10 percent by weight, the particles of metallic oxide comprise from 0.5 percent to 30 percent by weight of the emulsion, the oil phase comprises 5 percent to 30 percent by weight of the emulsion and an aqueous phase comprises at least 60 percent by weight of the emulsion.

In preferred embodiments of the product and the process of the invention the metallic oxide comprises an oxide of titanium, zinc or iron.

The average primary particle size of the particles of metallic oxide used to prepare the oil-in-water emulsion of the invention is less than 0.2 micron and where the particles are substantially spherical then this size will be taken to represent the diameter. However, the invention also encompasses particles of metallic oxides which are non-spherical and in such cases the average primary particle size refers to the largest dimension.

Preferably the average primary particle size of the particles is from 0.01 to 0.15 micron and more preferably from 0.01 to 0.06 micron when they are substantially spherical. Particularly useful products can be prepared using substantially spherical particles having an average primary particle size in the range 0.01 to 0.03 micron. For particles having an acicular shape the average largest dimension of the primary particles is preferably less than 0.15 micron and more preferably from 0.02 to 0.10 micron.

When the metallic oxide is titanium dioxide the particles are preferably acicular in shape and have a ratio of largest dimension to shortest dimension of from 8:1 to 2:1.

When the metallic oxide is zinc oxide the particles preferably have an average primary particle size of 0.005 to 0.15 micron and more preferably have an average primary particle size of 0.03 to 0.07 micron.

The particles of metallic oxide may comprise substantially pure metallic oxide but may also carry an inorganic coating or organic coating. For example, particles of titanium dioxide can be coated with oxides of other elements such as oxides of aluminium, zirconium or silicon and a form of acicular, coated titanium dioxide which is especially useful in the products of this invention is disclosed in UK Patent GB 2 205 088.

The particles of metallic oxides may also carry, if desired, a coating of one or more organic materials such as polyols, amines, alkanolamines, polymeric organic silicon compounds, hydrophilic polymers such as polyacrylamide, polyacrylic acid, carboxymethyl cellulose and xanthan gum or surfactants.

The emulsions of the current invention contain a relatively small amount of one or more emulsifiers by comparison with previously known emulsions. Preferably the total amount of emulsifiers present in the emulsion is less than 5% by weight. Also the quantity of hydrophilic emulsifiers present is preferably less than 10% by weight of the total quantity of emulsifiers present and, in the most preferred case, no hydrophilic emulsifiers are present.

Generally, the hydrophile-lipophile balance (HLB value) of the emulsifier system is less than 6 and, preferably, the HLB value is less than 5. This contrasts with the belief generally held heretobefore that an emulsifier suitable for forming an oil-in-water emulsion should have a higher HLB value (e.g. 8 to 18).

When hydrophilic emulsifiers are present then suitable emulsifiers include polyoxyethylene derivatives of sorbitan fatty acid esters, polyoxyethylene fatty acid esters, polyoxyethylene fatty ethers, phosphate esters, fatty alcohol sulphates, polyglycoside ethers, polyglycoside esters and alkali metal salts of sulphosuccinate esters.

Hydrophobic emulsifiers suitable for use in the products of the invention include lipid emulsifiers such as fatty alcohols, fatty acids, glyceryl esters, sorbitan esters, methylglycoside esters and sucrose esters. Generally, in contrast to hydrophilic emulsifiers these emulsifiers are easy to produce from renewable raw materials, are readily bio-degradable and do not contain toxic side products.

In carrying out the process of the invention an aqueous dispersion of a metallic oxide having a primary particle size as hereinbefore defined is used. Typically, the dispersion is prepared by milling the metallic oxide in water in the presence of a particulate grinding medium and in the presence of a dispersing agent.

UK Patent Application GB 2 226 018 discloses an aqueous dispersion of titanium dioxide having an acicular shape containing a dispersing agent which is a polycarboxylic acid or a salt thereof. The dispersions described in GB 2 226 018 are particularly suitable for use in the method of the current invention when it is desired to produce an oil-in-water emulsion containing titanium dioxide.

The technique described in GB 2 226 018 can be used to prepare aqueous dispersions of metallic oxides other than titanium dioxide which are suitable for use in the method of the invention.

Suitable dispersing agents which can be used to prepare dispersions of metallic oxides according to GB 2 226 018 include polyacrylic acids, substituted acrylic acid polymers, acrylic copolymers, sodium and/or ammonium salts of polyacrylic acids and sodium and/or ammonium salts of acrylic copolymers.

The total quantity of emulsifiers used is less than 10% by weight of the emulsion and suitable emulsifiers are as hereinbefore described.

The composition of the oil phase is chosen to suit the proposed use for the emulsion. For example, when the emulsion is intended for use as a sunscreen the oil phase will generally comprise paraffin oils, triglyceride esters, esters of fatty acids and fatty alcohols or silicone oils.

The aqueous dispersions of metallic oxide, emulsifier and oil phase are mixed under conditions which produce an oil-in-water emulsion.

In a typical process, the aqueous dispersion is mixed, if required, with other water miscible ingredients to form an aqueous phase and this phase and the oil phase are separately heated to at least 40° C., preferably to at least 60° C. and more preferably to at least 70° C. These two phases are then mixed under vigorous stirring in the presence of the emulsifier or emulsifiers. Mixing equipment which has found use for preparing cosmetic creams, lotions etc. is suitable for preparing the emulsions. High shear mixers/homogenisers are particularly suitable.

The emulsifier(s) are usually added to the aqueous phase before the oil phase is mixed with the aqueous phase.

Other ingredients can be added to the emulsion depending upon the intended use. These ingredients may be introduced in any convenient manner. For example they can be mixed with the emulsion or added to the aqueous dispersion or the oil phase before these components are mixed together. As examples, perfumes, antioxidants, moisturisers, thickeners and preservatives are normally added to emulsions which are intended for use as cosmetics.

The oil-in-water emulsions of this invention find use as sunscreens, as skin protectants, as moisturisers and as after-sun lotions and are particularly useful in preparing products which are transparent to visible light but absorbent to UV light. The emulsions can also be used in, for example, hair conditioners, hair sprays and pharamaceutical ointments.

The emulsions use smaller quantities of emulsifiers than known emulsions and the emulsifiers which are preferred are easily produced and readily bio-degradable.

The process of the invention enables emulsions with the above desirable properties to be produced and in which the selection of emulsifier(s) is less dependent upon the nature of the oil phase than hitherto.

Emulsions prepared according to the invention have been shown to possess better Sun Protection Factors (SPF values) than emulsions containing similar quantities of metallic oxide but prepared by previously known methods.

The invention is illustrated by the following examples.

| | | Parts by weight |
|---|---|---|
| 1) | Sorbitan Monostearate (sold under the | 4.00 |
| | trade name Span 60) | |
| 2) | Stearyl alcohol | 2.50 |
| 3) | Paraffin oil | 10.00 |
| 4) | Dispersion of titanium dioxide in water (sold under the trade name Tioveil AQ) | 12.50 |
| 5) | Glycerol | 4.00 |
| 6) | Carbomer 934 | 0.08 |
| 7) | Demineralised water | to 100 |

Ingredients 1 to 3 were mixed together and heated to 80° C. to form an oil component. Ingredients 4 to 7 were mixed together and also heated to 80° C. to form an aqueous component. The oil component was added to the aqueous component with intensive stirring (motor-driven paddle stirrer). The resulting emulsion was homogenised for two minutes using a high-shear mixer/homogeniser (Silverson), and then allowed to cool to room temperature with slow agitation. The resulting emulsion was stable for greater than two months at room temperature.

EXAMPLE 2

An suncream comprising an oil-in-water emulsion was prepared using the following formulation.

| | % by weight |
|---|---|
| Phase A | |
| Isopropyl Myristate | 4.00 |
| Mineral Oil | 6.50 |
| Grape Seed Oil | 2.50 |
| Stearyl Alcohol | 2.00 |
| Petrolatum | 2.00 |
| Phase B | |
| Sorbitan Stearate (Span 60[1]) | 6.00 |
| Disodium Ricinoleamido MEA-Sulfosuccinate (Rewoderm S 1333[2]) | 0.20 |
| Titanium Dioxide Aqueous Dispersion (Tioveil AQ[3]) | 15.00 |
| Glycerin | 4.00 |
| Allantoin | 0.20 |
| D-Panthenol[4] | 0.80 |
| Demineralised Water | 56.40 |
| Phase C | |
| 5-Chloro-2-methyl-4-isothiazolin-3-one (and) 2-methyl-4-isothiazolin-3-one (Kathon CG[5]) | 0.20 |
| Crematest S Timbuktu Perfume[6] | 0.20 |

Suppliers
[1]ICI Specialty Chemicals,
[2]REWO,
[3]Tioxide Specialties Limited,
[4]Hoffmann La Roche,
[5]Rohm & Haas,
[6]Dragoco.

Phase A (oil phase) and Phase B (aqueous phase) were separately heated to 80° C. Phase A was added to Phase B under intensive stirring (motor driven paddle stirrer). The resultant mixture was then homogenised by mixing for 1 minute in a domestic kitchen stirrer (Braun model 4169) and the homogenised mixture was allowed to cool with gentle agitation. Phase C was added to this mixture when the temperature reached 35° C. and agitation was stopped when the temperature fell to 25° C.

EXAMPLE 3

A suncream comprising an oil-in-water emulsion was prepared using the following formulation.

|  | % by weight |
|---|---|
| Phase A | |
| Isohexadecane (Arlamol HD[1]) | 6.00 |
| Octyl Stearate (Cetiol 868[6]) | 4.00 |
| Decyl Oleate (Cetiol V[6]) | 2.00 |
| Behenyl Alcohol | 1.00 |
| dl-α-Tocopheryl Acetate[4] | 1.00 |
| Phase B | |
| Sorbitan Stearate (Span 60[1]) | 6.00 |
| Disodium Ricinoleamido MEA-Sulfosuccinate (Rewoderm S 1333[2]) | 0.20 |
| Titanium Dioxide Aqueous Dispersion (Tioveil AQ[3]) | 10.00 |
| Allantoin | 0.20 |
| D-Panthenol[4] | 0.80 |
| Demineralised Water | 68.78 |
| Phase C | |
| 5-Chloro-2-methyl-4-isothiazolin-3-one (and) 2-methyl-4-isothiazolin-3-one (Kathon CG[5]) | 0.02 |

Suppliers
[1]ICI Specialty Chemicals,
[2]REWO,
[3]Tioxide Specialties Limited,
[4]Hoffmann La Roche,
[5]Rohm & Haas,
[6]Henkel The ingredients were mixed using the method described in Example 2.

EXAMPLE 4

A suncream comprising an oil-in-water emulsion was prepared using the following formulation.

|  | % by weight |
|---|---|
| Phase A | |
| Isopropyl Myristate | 3.00 |
| Mineral Oil | 6.00 |
| Grape Seed Oil | 2.00 |
| Stearyl Alcohol | 2.00 |
| dl-α-Tocopheryl Acetate[4] | 1.00 |
| Phase B | |
| Sorbitan Stearate (Span 60[1]) | 6.00 |
| Disodium Ricinoleamido MEA-Sulfosuccinate (Rewoderm S 1333[2]) | 0.20 |
| Tioxide Dioxide Aqueous Dispersion (Tioveil AQ[3]) | 5.00 |
| Glycerin | 4.00 |
| Allantoin | 0.20 |
| D-Panthenol[4] | 0.80 |
| Demineralised Water | 69.40 |
| Phase C | |
| 5-Chloro-2-methyl-4-isothiazolin-3-one (and) 2-methyl-4-isothiazolin-3-one (Kathon CG[5]) | 0.20 |
| Crematest S Timbuktu Perfume[6] | 0.20 |

Suppliers
[1]ICI Specialty Chemicals,
[2]REWO,
[3]Tioxide Specialties Limited,
[4]Hoffmann La Roche,
[5]Rohm & Haas,
[6]Dragoco The ingredients were mixed using the method described in Example 2.

EXAMPLE 5

A suncream comprising an oil-in-water emulsion was prepared using the following formulation.

|  | % by weight |
|---|---|
| Phase A | |
| Isopropyl Myristate | 4.00 |
| Mineral Oil | 6.50 |
| Grape Seed Oil | 2.50 |
| Stearyl Alcohol | 2.00 |
| Petrolatum | 2.00 |
| Phase B | |
| Sorbitan Stearate (Span 60[1]) | 5.00 |
| Titanium Dioxide Aqueous Dispersion (Tioveil AQ[3]) | 10.00 |
| Glycerin | 4.00 |
| Allantoin | 0.20 |
| D-Panthenol[4] | 0.80 |
| Demineralised Water | 62.60 |
| Phase C | |
| 5-Chloro-2-methyl-4-isothiazolin-3-one (and) 2-methyl-4-isothiazolin-3-one (Kathon CG[5]) | 0.20 |
| Crematest S Timbuktu Perfume[6] | 0.20 |

Suppliers
[1]ICI Specialty Chemicals,
[2]REWO,
[3]Tioxide Specialties Limited,
[4]Hoffmann La Roche,
[5]Rohm & Haas,
[6]Dragoco The ingredients were mixed using the method described in Example 2.

EXAMPLE 6

A sunlotion comprising an oil-in-water emulsion was prepared using the following formulation.

|  | % by weight |
|---|---|
| Phase A | |
| Caprylic/Capric Triglyceride (Miglyol 812N[6]) | 4.00 |
| Mineral Oil | 6.00 |
| Grape Seed Oil | 2.00 |
| Petrolatum | 2.00 |
| Stearyl Alcohol | 0.50 |
| dl-α-Tocopheryl Acetate[4] | 2.00 |
| Phase B | |
| Sorbitan Stearate (Span 60[1]) | 3.00 |
| Disodium Ricinoleamido MEA-Sulfosuccinate (Rewoderm S 1333[2]) | 0.20 |
| Titanium Dioxide Aqueous Dispersion (Tioveil AQ[3]) | 10.00 |
| Glycerin | 4.00 |
| Allantoin | 0.20 |
| D-Panthenol[4] | 0.80 |
| Demineralised Water | 65.28 |
| Phase C | |
| 5-Chloro-2-methyl-4-isothiazolin-3-one (and) 2-methyl-4-isothiazolin-3-one (Kathon CG[5]) | 0.02 |

Suppliers
[1]ICI Specialty Chemicals,
[2]REWO,
[3]Tioxide Specialties Limited,
[4]Hoffmann La Roche,
[5]Rohm & Haas,
[6]Huls The ingredients were mixed using the method described in Example 2.

EXAMPLE 7

A sunlotion comprising an oil-in-water emulsion was prepared using the following formulation.

|  | % by weight |
|---|---|
| Phase A | |
| Isohexadecane (Arlamol HD[1]) | 6.00 |
| Octyl Stearate (Cetiol 868[6]) | 4.00 |
| Decyl Oleate (Cetiol V[6]) | 2.00 |
| dl-α-Tocopheryl Acetate[4] | 1.00 |
| Phase B | |

|  | % by weight |
|---|---|
| Sorbitan Stearate (Span 60[1]) | 4.00 |
| Disodium Ricinoleamido MEA-Sulfosuccinate (Rewoderm S 1333[2]) | 0.20 |
| Titanium Dioxide Aqueous Dispersion (Tioveil AQ[3]) | 10.00 |
| Allantoin | 0.20 |
| D-Panthenol[4] | 0.80 |
| Demineralised Water | 71.78 |
| Phase C | |
| 5-Chloro-2-methyl-4-isothiazolin-3-one (and) 2-methyl-4-isothiazolin-3-one (Kathon CG[5]) | 0.02 |

Suppliers
[1]ICI Specialty Chemicals,
[2]REWO,
[3]Tioxide Specialties Limited,
[4]Hoffmann La Roche,
[5]Rohm & Haas,
[6]Henkel.

The ingredients were mixed using the method described in Example 2.

EXAMPLE 8

A sunlotion comprising an oil-in-water emulsion was prepared using the following formulation.

|  | % by weight |
|---|---|
| Phase A | |
| Caprylic/Capric Triglyceride (Miglycol 812N[6]) | 4.00 |
| Mineral Oil | 6.00 |
| Grape Seed Oil | 2.00 |
| Petrolatum | 2.00 |
| dl-α-Tocopheryl Acetate[4] | 2.00 |
| Phase B | |
| Sorbitan Stearate (Span 60[1]) | 3.00 |
| Disodium Ricinoleamido MEA-Sulfosuccinate (Rewoderm S 1333[2]) | 0.20 |
| Titanium Dioxide Aqueous Dispersion (Tioveil AQ[3]) | 10.00 |
| Glycerin | 4.00 |
| Allantoin | 0.20 |
| D-Panthenol[4] | 0.80 |
| Demineralised Water | 65.78 |
| Phase C | |
| 5-Chloro-2-methyl-4-isothiazolin-3-one (and) 2-methyl-4-isothiazolin-3-one (Kathon CG[5]) | 0.02 |

Suppliers
[1]ICI Specialty Chemicals,
[2]REWO,
[3]Tioxide Specialties Limited,
[4]Hoffmann La Roche,
[5]Rohm & Haas,
[6]Huls.

The ingredients were mixed using the method described in Example 2.

EXAMPLE 9

A sunlotion comprising an oil-in-water emulsion was prepared using the following formulation.

|  | % by weight |
|---|---|
| Phase A | |
| Caprylic/Capric Triglyceride (Miglycol 812N[6]) | 4.00 |
| Mineral Oil | 6.00 |
| Grape Seed Oil | 2.00 |
| Petrolatum | 2.00 |
| Isoamyl p-Methoxycinnamate (Neo Heliopan Type E 1000[7]) | 3.00 |
| dl-α-Tocopheryl Acetate[4] | 2.00 |
| Phase B | |
| Sorbitan Stearate (Span 60[1]) | 3.00 |
| Disodium Ricinoleamido MEA-Sulfosuccinate (Rewoderm S 1333[2]) | 0.20 |
| Titanium Dioxide Aqueous Dispersion (Tioveil AQ[3]) | 10.00 |
| Glycerin | 4.00 |
| Allantoin | 0.20 |
| D-Panthenol[4] | 0.80 |
| Demineralised Water | 62.78 |
| Phase C | |
| 5-Chloro-2-methyl-4-isothiazolin-3-one (and) 2-methyl-4-isothiazolin-3-one (Kathon CG[5]) | 0.02 |

Suppliers
[1]ICI Specialty Chemicals,
[2]REWO,
[3]Tioxide Specialties Limited,
[4]Hoffmann La Roche,
[5]Rohm & Haas,
[6]Huls,
[7]Haarmann & Reimer.

The ingredients were mixed using the method described in Example 2.

I claim:

1. An oil-in-water emulsion comprising from 0.5 percent to 30 percent by weight with respect to the total weight of emulsion of particles of a metallic oxide having an average primary particle size of less than 0.2 micron, said emulsion containing an emulsifier system comprising one or more emulsifiers, said emulsifier system being present in an amount of less than 10 percent by weight with respect to the total weight of emulsion and said emulsifier system having a hydrophile-lipophile balance of less than 6, from 5 percent to 30 percent by weight with respect to the total weight of emulsion of an oil phase and at least 60 percent by weight with respect to total weight of emulsion of an aqueous phase.

2. An oil-in-water emulsion according to claim 1 in which the metallic oxide is an oxide of a metal selected from the group consisting of titanium, zinc and iron.

3. An oil-in-water emulsion according to claim 1 in which the particles of metallic oxide are substantially spherical and have an average primary particle size of from 0.01 to 0.15 micron.

4. An oil-in-water emulsion according to claim 3 in which the average primary particle size is from 0.01 to 0.06 micron.

5. An oil-in-water emulsion according to claim 3 in which the average primary particle size is from 0.01 to 0.03 micron.

6. An oil-in-water emulsion according to claim 1 in which the particles of metallic oxide have an acicular shape and have an average largest dimension of the primary particles of less than 0.15 micron.

7. An oil-in-water emulsion according to claim 6 in which the average largest dimension of the primary particles is from 0.02 to 0.10 micron.

8. An oil-in-water emulsion according to claim 6 in which the metallic oxide is titanium dioxide and the primary particles have a ratio of longest dimension to shortest dimension in the range of from 8:1 to 2:1.

9. An oil-in-water emulsion according to claim 1 in which the metallic oxide is zinc oxide having an average primary particle size of from 0.005 to 0.15 micron.

10. An oil-in-water emulsion according to claim 9 in which the average primary particle size is from 0.03 to 0.07 micron.

11. An oil-in-water emulsion according to claim 1 in which the particles of metallic oxide carry an inorganic or an organic coating.

12. An oil-in-water emulsion according to claim 11 in which the metallic oxide is titanium dioxide and the particles carry a coating of an oxide of an element selected from the group consisting of aluminium, zirconium and silicon.

13. An oil-in-water emulsion according to claim 11 in which the particles of metallic oxide carry a coating of an organic compound selected from the group consisting of polyols, amines, alkanolamines, polymeric silicon compounds, polyacrylamide, polyacrylic acid, carboxymethyl cellulose, xanthan gum and surfactants.

14. An oil-in-water emulsion according claim 1 in which the total amount of emulsifiers present in the emulsion is less than 5 percent by weight with respect to weight of emulsion.

15. An oil-in-water emulsion according to claim 1 in which less than 10 percent by weight of the total quantity of emulsifiers present comprises hydrophilic emulsifiers.

16. An oil-in-water emulsion according to claim 1 in which no hydrophilic emulsifiers are present.

17. An oil-in-water emulsion according to claim 1 in which the hydrophile-lipophile balance of the emulsifier system is less than 5.

18. An oil-in-water emulsion according to claim 1 in which at least one of the emulsifiers present is selected from the group consisting of polyoxyethylene derivatives of sorbitan fatty acid esters, polyoxyethylene fatty acid esters, polyoxyethylene fatty ethers, phosphate esters, fatty alcohol sulphates, polyglycoside ethers, polyglycoside esters and alkali metal salts of sulphosuccinate esters.

19. An oil-in-water emulsion according to claim 1 in which at least one of the emulsifiers present is selected from the group consisting of fatty alcohols, fatty acids, glyceryl esters, sorbitan esters, methylglycoside esters and sucrose esters.

20. An oil-in-water emulsion according to claim 1 in which the oil phase comprises an oil selected from the group consisting of paraffin oils, triglyceride esters, esters of fatty acids and fatty alcohols and silicone oils.

21. A process for preparing an oil-in-water emulsion comprising forming an aqueous dispersion of particles of a metallic oxide having an average primary particle size of less than 0.2 micron and mixing said dispersion with one or more emulsifiers and an oil phase under conditions in which an oil-in-water emulsion is formed wherein the total amount of emulsifiers present in the oil-in-water emulsion so formed is less than 5 percent by weight, the particles of metallic oxide comprise from 0.5 percent to 30 percent by weight of the emulsion, the oil phase comprises 5 percent to 30 percent by weight of the emulsion and an aqueous phase comprises at least 60 percent by weight of the emulsion.

22. A process according to claim 21 in which the aqueous dispersion of metallic oxide is prepared by milling the metallic oxide in water in the presence of a particulate grinding medium and in the presence of a dispersing agent.

23. A process according to claim 22 in which the dispersing agent is selected from the group consisting of polycarboxylic acids and salts thereof.

24. A process according to claim 23 in which the dispersing agent is selected from the group consisting of polyacrylic acids, substituted acrylic acid polymers, acrylic copolymers, sodium salts of polyacrylic acids, ammonium salts of polyacrylic acids, sodium salts of acrylic copolymers and ammonium salts of acrylic copolymers.

25. A process according to claim 23 in which the particles of metallic oxide are acicular particles of titanium dioxide.

26. A process according to claim 21 in which an aqueous phase comprising the aqueous dispersion and an oil phase are separately heated to a temperature of at least 40° C. and mixed in the presence of one or more emulsifiers with vigorous stirring.

27. A process according to claim 26 in which the aqueous phase and the oil phase are separately heated to at least 60° C.

28. A process according to claim 27 in which the aqueous phase and the oil phase are separately heated to at least 70° C.

29. A process for preparing an oil-in-water emulsion comprising forming an aqueous dispersion of particles of a metal oxide having an average primary particle size of less than 0.2 micron and mixing said dispersion with an emulsifier system comprising one or more emulsifiers and an oil phase under conditions in which an oil-in-water emulsion is formed wherein the total amount of emulsifiers present in the oil-in-water emulsion so formed is less than 10 percent by weight and the emulsifier system has a hydrophile-lipophile balance of less than 6, the particles of metallic oxide comprise from 0.5 percent to 30 percent by weight of emulsion, the oil phase comprises 5 percent to 30 percent by weight of the emulsion and an aqueous phase comprises at least 60 percent by weight of the emulsion.

* * * * *